(12) United States Patent
Bergman et al.

(10) Patent No.: US 6,248,742 B1
(45) Date of Patent: Jun. 19, 2001

(54) USES OF INDOLO-(2,3B)-QUINOXALINES

(75) Inventors: Jan Bergman, Spånga; Lennart Möller, Älvsjö; Hans Vallberg, Stockholm, all of (SE)

(73) Assignee: Leif J. I. Lundbald, Stockholm (SE)

( * ) Notice: Subject to any disclaimer, the term of this patent is extended or adjusted under 35 U.S.C. 154(b) by 0 days.

(21) Appl. No.: 08/881,389

(22) Filed: Jun. 24, 1997

Related U.S. Application Data

(63) Continuation-in-part of application No. PCT/SE95/01581, filed on Dec. 22, 1995.

(30) Foreign Application Priority Data

Dec. 27, 1994 (SE) ..................................................... 9404525

(51) Int. Cl.⁷ ......................... A61K 31/495; A61K 31/50
(52) U.S. Cl. .............................................................. 514/250
(58) Field of Search ............................................... 514/250

(56) References Cited

U.S. PATENT DOCUMENTS

4,990,510 * 2/1991 Bergman et al. ..................... 514/250
5,866,575 * 2/1999 Bergman ............................. 514/250

* cited by examiner

*Primary Examiner*—Jerome D. Goldberg
(74) *Attorney, Agent, or Firm*—Browdy and Neimark (57) ABSTRACT

Use of compounds of the formula I

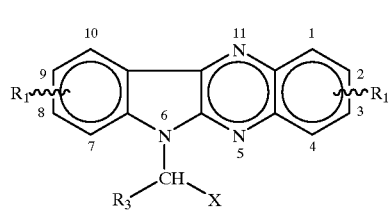

for preparing a medicated for protecting DNA in the initial phase and/or the prompting phase of carcinogenesis and for preventing oxidating stress in patients with diseases related to free radicals are described.

5 Claims, 7 Drawing Sheets

FIG. 2a
ANTIMUTAGENICITY OF B-220

(○) CELLS + PMA (5×10⁻⁸M)
(●) CELLS + -ll- + (DMSO 0.2%)
(▽) CELLS + -ll- + (DMSO 0.4%)
(▼) CELLS + -ll- + (DMSO 0.2% + 10μg ml, B220 SALT)
(□) CELLS + -ll- + (DMSO 0.3% + 15μg ml, B220 SALT)
(■) CELLS + -ll- + (DMSO 0.4% + 20μg ml, B220 SALT)

USES OF INDOLO-(2,3B)-QUINOXALINES

CROSS-REFERENCE TO RELATED APPLICATION

This is a CIP of parent, co-pending application PCT/SE95/01581, filed Dec. 22, 1995, the entire contents of which are hereby incorporated by reference.

The present invention relates to new uses of indolo-[2,3b]-quinoxalines of the general formula I wherein $R_1$ represents hydrogen or one or several, preferably 1 to 4, similar or different substituents in the positions 1–4 and/or 7–10, selected from halogen, preferably Br, lower alkyl/alkoxy group having not more than 4 carbon atoms, trifluoromethyl group, trichloromethyl group; and in one of the positions 7–10 $R_1$ can be a hydroxyl group;

- X is a group —$(CH_2)_n$—$R_2$ wherein $R_2$ represents a nitrogen containing basic residue such as $NH_2$, $NHR_4$ or $NR_5R_6$ wherein $R_4$, $R_5$ and $R_6$ independently are lower alkyl or cycloalkyl and n is an integer of from 1 to 4 and $R_3$ represents hydrogen, lower alkyl/cycloalkyl group having not more than 4 carbon atoms, and the physiologically acceptable addition products of the compounds with acids and halogen adducts, preferably adducts with iodine, iodine monochloride or iodine monobromide,
- as DNA protecting agent both in the initial phase and in the promoting phase of carcinogenesis and which agent also reduces or eliminates the effect of promoters and which agent has effects which protect for oxidative stress and effects of gamma-irradiation. Thus, the compounds used according to the present invention activates the defence of the body against carcinogenesis, oxidative stress and gamma-irradiation.

It is known that free radicals (oxidative stress) of different types are associated with a range of diseases such as ischemic or reperfusion injury, thrombosis and embolism, atherosclerosis, allergic/inflammatory conditions such as bronchial asthma and rheumatoid arthritis, diseases caused by ionizing radiation or ultra violet light, conditions related to neurodegenerative diseases for instance Parkinson's disease and Alzheimer's disease, ageing, apoptosis, necrosis and cirrhosis, cataract, physical stress, diabetes, autoimmune diseases, intoxications, colitis, hematocrosis, neoplasms and toxicity of antineoplastic or immuno suppressive agents diseases, premature aging or consequences of viral or bacterial infections and endogeneous or exogeneous chemicals present in air, food, general environmental contamination or lifestyle related exposure. An explanation for these conditions and diseases can be that the endogeneous protecting capacity are not sufficiently active to protect the tissue against radical damage. Lipid peroxidation or DNA-oxidation caused by excess generation of radicals can constitute significant damaging pathways in the above conditions and diseases. The compounds used according to the present invention probably enter into the cell where it activates parts of the genome.

Oxidative stress can be chemically, physically or biologically induced. Chemically induced oxidative stress is caused by a compound which gives rise to a tissue damage. Physically induced stress is caused by e.g. 1) radiation, such as radioactive or ionizing radiation or UV radiation; 2) by physical blockage of blood flow; biologically induced oxidative stress is the defence by the body itself, with over-reaction of oxidases in phagocytes, extra and intra cellular, one example is HIV patients. Other examples are asthma, rheumatoid arthritis, diabetes etc, cf. above.

Different conditions such as inflammations, infections, gamma-radiation, UV radiation and deficiency of vitamins/antioxidants give rise to oxidative stress which leads to the different conditions and diseases stated above. Use of the compounds according to the present invention in preparations to be administrated via different carriers will thus protect the body against oxidative stress and prevent the outburst of different diseases caused by such oxidative stress.

Indolo-[2,3b]-quinoxalines of the general formula I wherein $R_1$ is a hydroxyl group in one of the positions 7–10 are prepared by means of a process described in the following section. Especially compounds wherein $R_1$ is a hydroxyl group in position 9 show interesting properites for the use according to the present invention.

Substituted indolo-quinoxalines of formula I have previously been demonstrated to possess valuable activity against several types of virus and several of the compounds also have been demonstrated to show a potent anti-cancer effect, cf. our previous patent EP 0 238 459 and U.S. Pat. No. 4,990,510. Furthermore, they have also been shown to be inactive as enzyme inhibitors, cf. Harmenberg et al, Antimicrobial agents and chemotherapy, November 1988, pp 1720–1724.

Indolo-quinoxaline derivatives hydroxylated in the positions 7, 8, 9 or 10, especially in position 9, are of interest as metabolites or possible metabolites to biologically active quinoxaline derivatives such as 1b. Such hydroxylated derivatives possess interesting anti viral and anti cancer properties in addition to their effect as DNA protecting agents and their effects to protect from oxidative stress.

The hydroxylated substances according to the present invention cannot be made by means of the methods described in our above mentioned patents. Thus, reaction of phenylene diamines and methoxyisatin, such as shown in Scheme 1, does not give indoloquinoxalines but spirocyclic substances which cannot be converted to the desired substances.

Scheme I

Hydroxylation according to Scheme 2 does not function either

Scheme 2

-continued

A compound of the general formula II can be prepared by subjecting a compound of the general formula III to mononitration with one equivalent of potassium nitrate or sodium nitrate in sulfuric acid whereby a compound according to the general formula IV is obtained, which latter compound by catalytic hydrogenation followed by diazotization with nitrous acid and then conversion of the diazonium ion obtained to the 9-OH group by treatment with a Cu-based catalyst composed of Cu$(NO_3)_2$ and $Cu_2O$ is converted to the compound of formula II.

This process is illustrated in the following scheme 3

Scheme 3

1a $R_1$ = H, $R_2$ = H
1b $R_1$ = Me, $R_2$ = H
1c $R_1$ = H, $R_2$= $CH_2CH_2NMe_2$
1d $R_1$ = Me, $R_2$= $CH_2CH_2NMe_2$

The preparation of these compounds according to the invention is illustrated in the following examples 1–5.

The compounds used according to the present invention unexpectedly have been found to possess a number of specific properties. Thus, they are not mutagenic or carcinogenic and they do not induce preneoplastic lesions and have not a DNA adduct forming activity. The in vivo toxicity in mammals is extremely low. Furthermore, the compounds used in the present invention reduce the spontaneous mutation frequency in the Salmonella assay.

The compounds do not induce oxidative stress, they reduce or even inhibit oxidative stress in vivo and down-regulate oxidative stress below control values.

The compounds are thus useful for reducing or eliminating oxidative stress induced by chemicals and for down-regulating an over-reaction by the immune system. Furthermore, the compounds are useful for activating the cellular defense system, i.e. the cells own protection for infections and inflammations.

The compounds can be used in combination with drugs to reduce side effects lika mutagenicity (chemotherapy, drugs for AIDS treatment), oxidative stress (amines and nitro compounds) and over-reactions of the immune system.

Another important use of the compounds is to prevent for negative health effects induced by UV light, i.e. sun radiation. Examples of these are inflammations, DNA lesions and free radicals. A further important use of the compounds is to slow down the Dorian-Gray syndrome (premature aging induced by oxidative stress) in HIV/AIDS patients.

A further object of the invention is the use of the compounds to increase the body weight when medical treatment/disease leads to loss of body weight. Examples are chemotherapy, irradiation and HIV/AIDS.

Another object according to the invention is the use of the compounds for treatment of human beings and animals after accidental exposure of irradiation to down-regulate oxidative stress and activate cellular defense processes.

A further important object according to the invention is the use of the compounds to reduce extracellular leakage of oxygen radicals from phagocytes that induces tissue damage during viral and bacterial infections.

Another important use according to the invention of the compounds is to protect lymphocytes that are exposed to neutrophiles (phagocytes), leaking free radicals into the blood stream. Thus, an over-reaction by neutrophiles in the blood stream leads to a leakage of free radicals that can induce apoptosis in lymphocytes and thereby lower the natural protection the lymphocytes are responsible for, i.e. an increased risk for infections. This is of special importance when the use of chemotherapy for tumor treatment is limited by the destruction of lymphocytes or during massive infections of viruses (for instance HIV) or bacteria. Also accidents in exposure at high concentrations of xenobiotics, high levels of radiation or burn wound induced oxidative stress can induce the destruction of lymphocytes due to leakage of free radicals from phagocytes during the critical and acute phase.

In addition, the compounds eliminate the mutagenicity of certain mutagens in the Salmonella test while the mutagenic effect of others are reduced, i.e. they are antimutagens.

Well known chemical substances which are mutagens and which thus initiate the tumor process (carcinogenesis) are polycyclic aromatic hydrocarbons (PAH), nitrated PAH compounds (nitro PAH) e.g. 2-nitrofluorene (NF); nitrosamines; different alkylating agents, food mutagens etc.

Furthermore, both UV radiation and gamma radiation (X-ray) have mutagenic effect and certain metals can catalyze reactions involving formation of DNA-damage.

In the first step in chemical carcinogenesis DNA adducts are formed. A characteristic feature of the compounds used according to the present invention is that they do not form DNA adducts. Furthermore, the compounds used according to the present invention reduce the capability of certain potent mutagens to form DNA adducts while other mutagens are less affected.

As regards the formation of early stages of tumor formation (preneoplastic foci) (in vivo) it has been found that the compounds used according to the present invention do not form any foci and furthermore reduce the capacity of potent carcinogens to form foci.

The compounds used according to the present invention have been tested as regards the formation of tumors (skin tumors) for mice subjected to strong tumor initiating and strong tumor promotion conditions. In this test model it was found that the compounds tested do not give rise to any tumors and furthermore if a compound according to the present invention was given twice a week the mice did not develop tumors which means that in the presence of a compound according to the present invention neither the very strong tumor initiating nor the very strong tumor promotion will lead to tumors. Furthermore, if the administration of the compound used according to the present invention is terminated the animals will develop the same amount of tumors as in the positive control. This means that the original DNA injury remains and the tumor promotor which is administrated continously can give rise to a considerable development of tumors. Accordingly a compound used according to the present invention can stop the tumor process caused by potent tumor promoting agents in combination with potent tumor initiators.

As regards toxic effects of the compounds used according to the present invention no such effects have been noted in vivo. The oral $LD_{50}$ value is above 800 mg/kg body weight in rats, corresponding to a dose of 56 g to a human (70 kg).

In the promotion phase of carcinogenesis there are also chemical compounds which are known to be very potent promoters. One of the most potent promotors known today is triphorbolester (TPA). When testing a compound used according to the present invention by administration to an animal given TPA it was found that the effect of this promotor was eliminated.

The invention is illustrated by means of the following examples wherein examples 1–6 describe the preparation of intermediates and of compounds used according to the invention and examples 7–13 describe tests carried out with the compounds according to the invention.

EXAMPLE 1

2,3-dimethyl-6(2-dimethylaminoethyl)-9-nitro-6H-indolo[2,3-b]-quinoxaline (2d)

To a solution of 15.9 g (50 mmol) of (1d) in 200 ml concentrated $H_2SO_4$ 5.06 g (50 mmol) $KNO_3$ were added batchwise so that the temperature did not exceed 10° C. The solution was left with stirring at 5–10° C. in 2 h and then was poured onto ice-water. The mixture was made alkaline with 20% KOH-solution. This resulted in a yellow percipitate which was filtered off. The raw product was recrystallized from EtOH which gave 13.1 g of (2d).

Yield: 72%; M.P.: 219° C.; NMR: $\delta_H$(DMSO): 9.1 (1H, s, Ar), 8.6 (1H, d, Ar), 8.1 (1H, s, Ar), 8.1 (1H, d, Ar), 7.9 (1H, s, Ar), 4.6 (2H, t, $CH_2$), 2.8 (2H, t, $CH_2$), 2.5 (3H, s, $CH_3$), 2.5 (3H, s, $CH_3$), 2.2 (6H, s, $CH_3$) ppm. IR: $v_{max}$: 2940, 2760, 1620, 1580, 1510, 1460 br, 1320 br, 1190 br, 1135, 1100, 870, 810, 750, and 680 cm$^{-1}$.

EXAMPLE 2

6-(2-dimethylaminoethyl)-9-nitro-6H-indolo[2,3-b]-quinoxaline (2c)

(2c) was synthetisized in the same manner as (2d).

Yield: 86% (not recrystallized); M.p.: 206–08° C.; NMR: $\delta_H$(DMSO): 9.1 (1H, s, Ar), 8.8 (1H, d, Ar), 8.4 (1H, d, Ar), 8.2 (1H, d, Ar), 8.1 (1H, d, Ar), 7.8–8.0 (2H, dt, Ar), 4.7 (2H, t, $CH_2$), 2.8 (2H, t, $CH_2$), 2.2 (6H, s, $CH_3$) ppm. IR: $v_{max}$: 3060, 2940, 2810, 2770, 1610, 1580, 1510, 1465 br, 1400, 1330 br, 1300, 1245, 1145, 1125, 1105, 1070, 1045, 960, 915, 835, 795, 760, 750, 730, 710 cm$^{-1}$.

EXAMPLE 3

9-amino-2,3-dimethyl-6-(2-dimethylaminoethyl)-6H-indolo[2,3-b]-quinoxaline (3d)

A suspension of 3.63 9 (10 mmol) of (2d) and 0.36 g 10% Pd/C in 160 ml DMA was left under 2.7 atm hydrogen pressure for 24 h. The product was soluble in DMA. Pd/C was filtered away with celite. The filtrate was poured onto ice-water and pH was increased to basic with 20% KOH, which resulted in a brown precipitate. The precipitate was chromatographied in 20% MeoH/$CH_2Cl_2$, which resulted in 2.80 g of the product (3d).

Yield: 84%; M.P.: 250–51° C.; NMR: $\delta_H$(DMSO): 7.9 (1H, s, Ar), 7.8 (1H, s, Ar), 7.5 (1H, s, Ar), 7.4 (1H, d, Ar), 7.1 (1H, d, Ar), 5.1 (2H, br, $NH_2$), 4.4 (2H, t, CH2), 2.7 (2H, t, $CH_2$), 2.5 (3H, s, $CH_3$), 2.5 (3H, s, $CH_3$), 2.2 (6H, s, $CH_3$) ppm. $\delta_c$(DMSO): 145.0 (s), 143.3 (s), 138.7 (s), 138.6 (s), 137.1 (s), 136.0 (s), 135.0 (s), 128.0 (d), 126.5 (d), 119.5 (s), 119.0 (d), 110.6 (d), 105.4 (d), 56.7 (t), 45.2 (q), 38.9 (t), 19.9 (q), 19.6 (q) ppm. IR: $v_{max}$: 3390, 3320, 3200, 2960, 2940, 2920, 2820, 2770, 1580, 1480, 1400, 1330, 1190 br, 870, 810, 720, and 680 cm$^{-1}$.

EXAMPLE 4

2,3-dimethyl-6-(2-dimethylaminoethyl)-9-hydroxy-6H-indolo[2,3-b]-quinoxaline (4d)

660 mg (2 mmol) of (3d) were dissolved in 6 ml 30% $H_2SO_4$ at 15° C. The solution was cooled to 5° C. A solution of 179 mg (2.6 mmol) of $NaNO_2$ in 2 ml $H_2O$ was added without increasing the temperature above 5° C. After 30 minutes urea was added in order to consume unreacted $NaNO_2$. To the solution at zero degree Centigrade was added a zero degree $Cu(NO_3)_2$-solution (4 g $Cu(NO_3)_2.3H_2O$ in 50 ml $H_2O$) and then 286 mg $Cu_2O$ were added. This resulted in a strong formation of $N_2$-gas. When $N_2$ gas formation stopped the mixture was left in 30 minutes and then pH was increased to weakly alkaline. The mixture was extracted with $CH_2Cl_2$. the $CH_2Cl_2$ phase was dried and roll-evaporated. The raw product formed was chromatographated in 10% MeOH/$CH_2Cl_2$ which resulted in 133 mg of the desired product (4d).

Yield: 20%; M.p.: >260° C.; NMR: $\delta_H$(DMSO): 9.5 (1H, s, OH), 8.0 (1H, s, Ar), 7.8 (1H, s, Ar), 7.6 (1H, s, Ar), 7.6 (1H, d, Ar), 7.2 (1H, d, Ar), 4.5 (2H, t, $CH_2$), 2.7 (2H, t, $CH_2$), 2.5 (3H, s, $CH_3$), 2.5 (3H, s, $CH_3$), 2.2 (6H, s, $CH_3$). $\delta_C$(DMSO): 152.0 (s), 138.9 (s), 138.7 (s), 138.3 (s), 137.3 (s), 137.2 (s), 135.3 (s), 128.0 (d), 126.6 (d), 119.5 (d), 111.1 (d), 106.7 (d), 56.8 (t), 45.3 (q), 39.7 (t), 19.9 (q), 19.6 (q) ppm. IR: $v_{max}$: 3420 (br), 3130 (br), 2940, 2765, 1585, 1490, 1425, 1350, 1240, 1210, 1155, 1025, 1000, 865, and 725 cm.

EXAMPLE 5

9-Amino-6-(2-dimethyl-aminoethyl)-6H-indolo[2,3-b]-quinoxaline

Yield: 85%; M.p.: 222–223° C.; NMR: δH(DMSO): 8.2 (1H, d, Ar), 8.0 (1H, d, Ar), 7.7 (1H, dd, Ar), 7.6 (1H, dd, Ar), 7.5 (1H, s, Ar), 7.5 (1H, d, Ar), 7.1 (1H, d, Ar), 5.3 (2H, br, $NH_2$), 4.5 (2H, t, $CH_2$), 2.8 (2H, t, $CH_2$), 2.3 (6H, s, $CH_3$)

ppm. $\delta_C$(DMSO): 145.1 (s), 143.6 (s), 139.7 (s), 139.7 (s), 138.1 (s), 136.2 (s), 128.9 (d), 128.4 (d), 127.2 (d), 125.3 (d), 119.4 (d), 119.2 (s), 110.8 (d), 105.6 (d), 56.2 (t), 44.8 (q), 38.6 (t) ppm. IR: $v_{max}$: 3405, 3362, 3329, 3054, 2964, 2943, 2920, 2816, 2767, 1582, 1494, 1411, 1324, 1125, 809, 766, 621 and 592 cm$^{-1}$.

EXAMPLE 6

6-(2-dimethylaminoethyl)-9-hydroxy-6H-indolo[2,3-b]-quinoxaline

Yield: 18%; M.p.: 269–270° C.; NMR: $\delta_H$(DMSO): 9.6 (1H, S, OH), 8.2 (1H, d, Ar), 8.0 (1H, d, Ar), 7.8 (1H, dd, Ar), 7.6–7.7 (2H, m, Ar), 7.6 (1H, d, Ar), 7.2 (1H, d, Ar), 4.5 (2H, t, CH$_2$), 2.7 (2H, t, CH$_2$), 2.2 (6H, s, CH$_3$). $\delta_C$(DMSO): 152.1 (s), 145.2 (s), 139.8 (s), 139.4 (s), 138.2 (s), 137.7 (s), 128.9 (d), 128.7 (d), 127.3 (d), 125.5 (d), 119.9 (d), 119.1 (s), 111.2 (d), 106.8 (d), 56.7 (t), 45.2 (q), 39.1 (t) ppm. IR: $v_{max}$: 3127 br, 2964, 2941, 2771, 1586, 1489, 1425, 1261, 1239, 1210, 1119, 1048, 1021, 805 and 756 cm$^{-1}$.

EXAMPLE 7

Figure 1A:
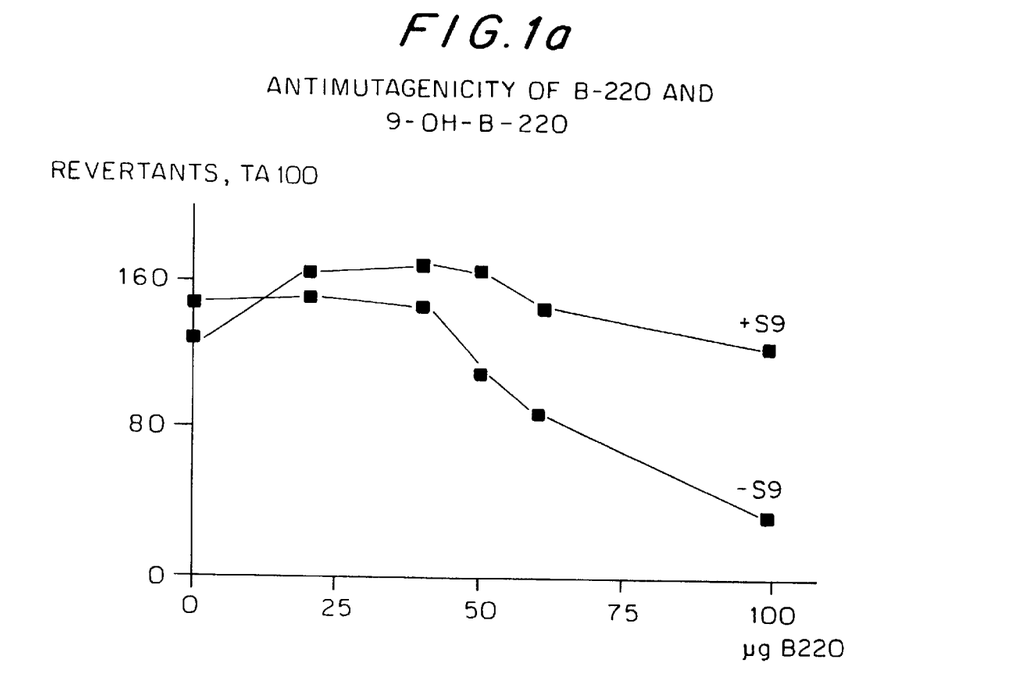
FIG. 1a illustrates the antimutagenicity of B-220.
Figure 1B:
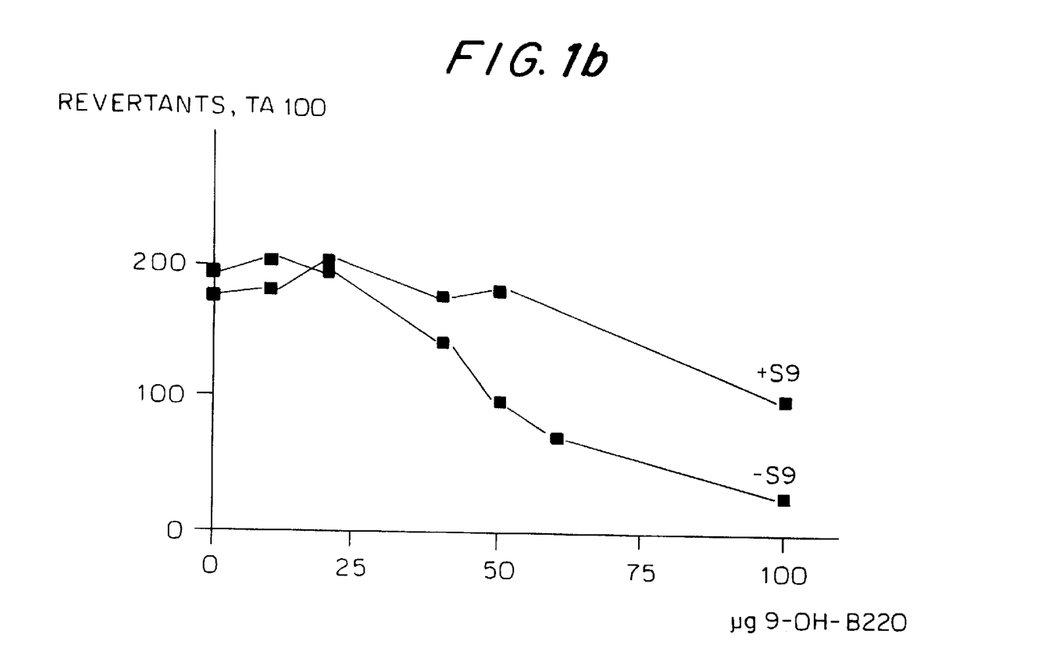
FIG. 1b illustrates the antimutagenicity of 9-OH-B-220.

This example illustrates the mutagenic potential in the bacterial mutagenicity test, "Ames test", with test strain TA100, of B-220 (FIG. 1a) and 9-OH-B-220 (FIG. 1b). S9 indicates the presence (+S9) or absence (−S9) of a cellular enzymatic fraction capable to metabolize the tested substances. The metabolic activation is a liver fraction containing enzymes needed in metabolism. The results are shown in FIGS. 1a and 1b. In the Figures revertants/plate, an intensity measurement of mutagenic activity, is plotted against μg B-220 and μg 9-OH-B-220.

The results show that the substances are non-mutagenic but also anti-mutagenic (reduces the spontaneous background). The anti-mutagenic potential is similar for B-220 and 9-OH-B-220.

EXAMPLE 8

The following example illustrates the fact that the compound B-220 reduces the mutagenicity of potent mutagens in the bacterial mutagenicity test, the "Ames test". In the test the bacterial strain TA 100 was used. In the experiments two strong mutagens were used with and without the addition of B-220. These mutagens were MMS= Methylmethanesulphonate and EMS= Ethylmethanesulphonate. The results of the experiments carried out are shown graphically in FIG. 2a and 2b. In the Figures revertants/plate, is plotted against microgram MMS and EMS, respectively, plus 70 μg B-220.

Figure 2A:
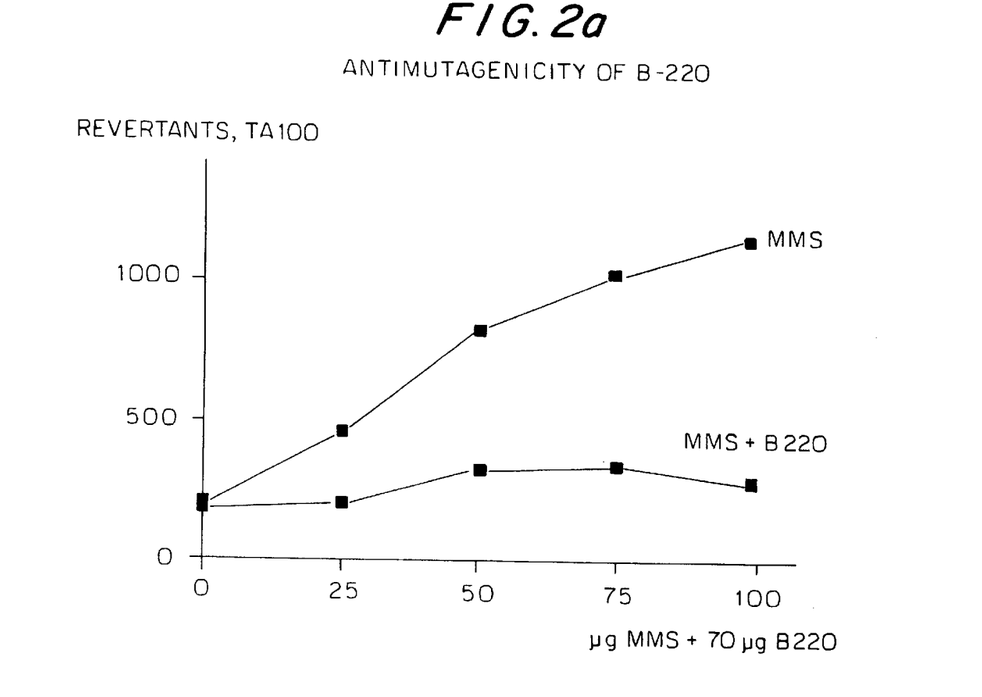
FIG. 2a illustrates the antimutagenicity of B-220 plus MMS.

From FIG. 2a it can be seen that MMS is a strong mutagen but when B-220 is added the mutagenicity disappears.

Figure 2B:
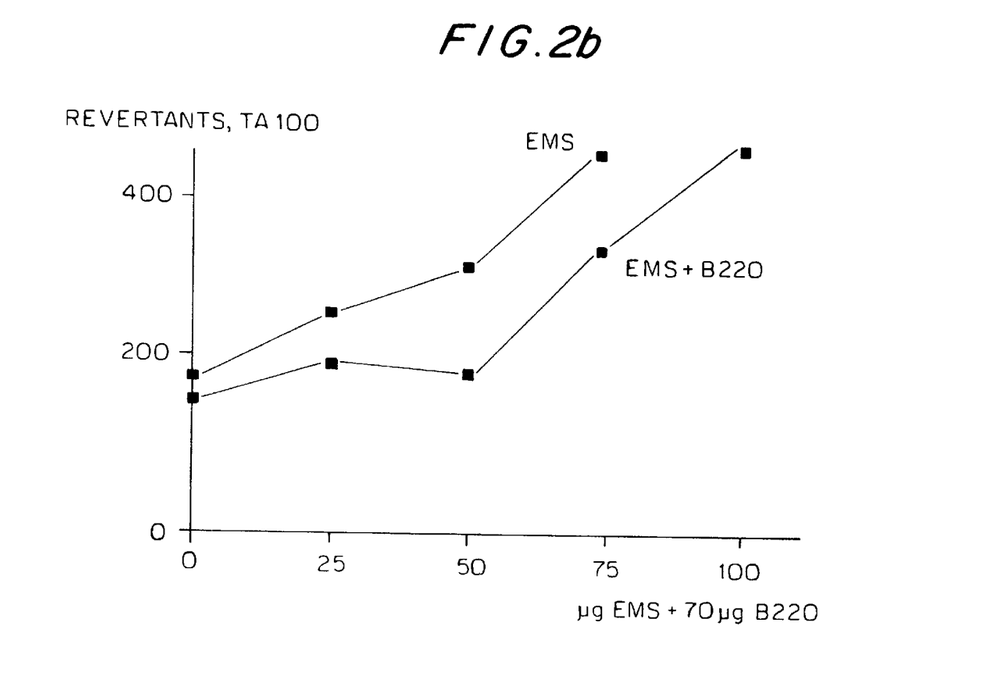
FIG. 2b illustrates the antimutagenicity of B-220 plus EMS.

From FIG. 2b it can be seen that EMS is a strong mutagen but needs other routes for DNA repair compared to MMS. The addition of B-220 reduce the mutagenicity but not as much as for MMS.

These tests show that strong mutagens are not able, or reduced in their capacity to generate mutations when B-220 is present. The reduction of mutagenicity is not caused by cell death since tested substances behave differently (mechanistic reason).

EXAMPLE 9

The in vivo toxicity of B-220 was tested in rats. A portion of the liver was removed (partial hepatectomy, PH) by surgery and the regeneration of liver tissue was studied. The regeneration was measured as liver-somatic index (LSI), in other words the relative liver weight in per cent of the body weight.

AAF (2-acetylaminofluorene) is a very toxic substance which acts as a mito-inhibitor, i.e. inhibits cell division of normal liver cells.

Figure 3:
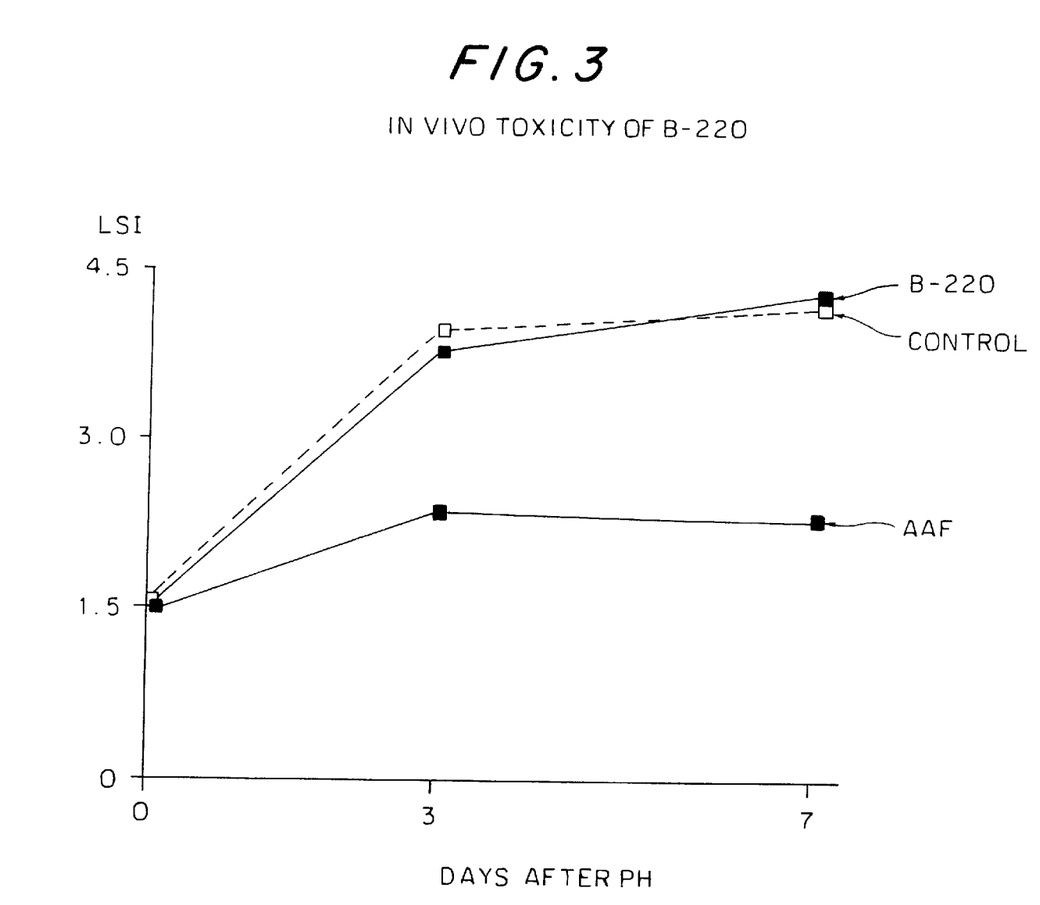
FIG. 3 illustrates the in vivo toxicity of B-220.

The results are shown in FIG. 3 wherein LSI is plotted against days after partial heptatectomy.

As seen from FIG. 3 the regeneration of liver tissue in the AAF group was very slow. The control group recieved nothing and there was a rapid regeneration of tissue. In the group administered B-220 no difference from the controls could be seen. B-220 did not show any toxic effects to rats in vivo measured during very intensive cell division.

From these results it can be seen that B-220 is not toxic in vivo to cells that undergo cell division.

EXAMPLE 10

Figure 4:
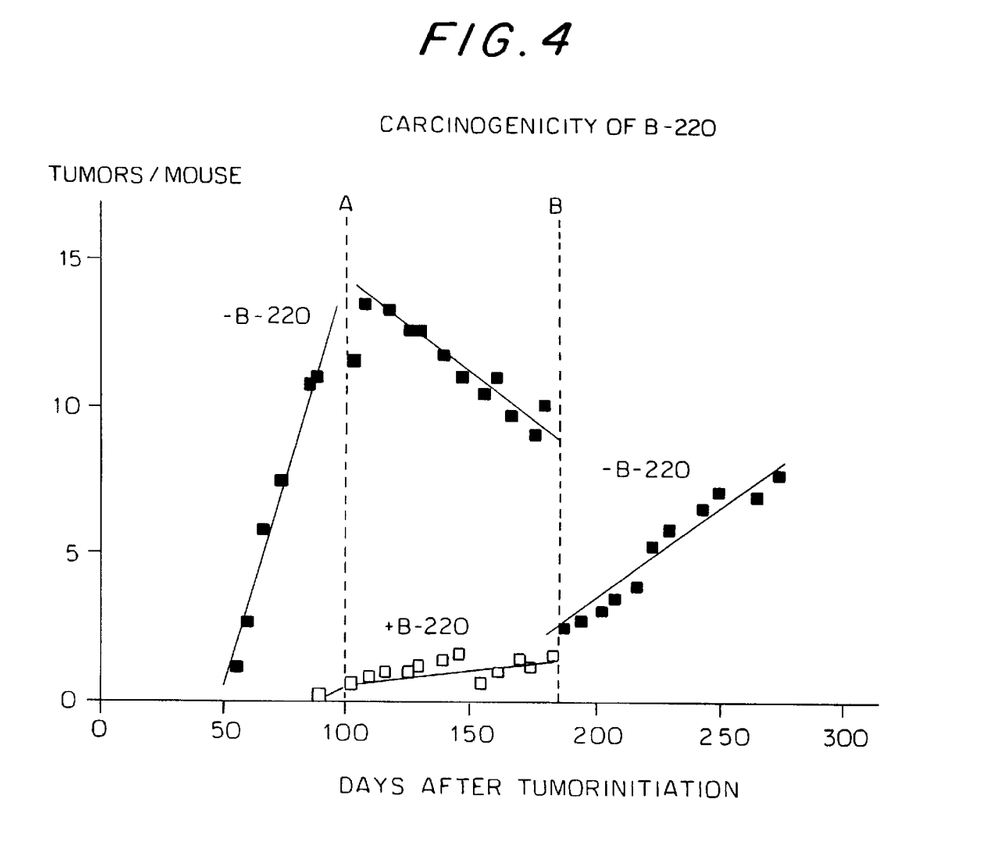
FIG. 4 illustrates the carcinogenicity of B-220.

This example illustrates a tumor model which is based on in vivo tumor initiation with one dose of dimethylbenzanthracene (DMBA) whereafter a potent tumor promotor triphorbol ester (TPA) was administered twice a week. After a number of weeks the skin tumors can be detected and followed during the study. After approximately 100 days (A) the positive controls reaches the maximum, whereafter the total number declines due to the behavior of the animals. In the group administered B-220 one hour before TPA there were no tumors at all at the same time point. After six months—the normal time for termination in this model—the B-220 group had developed a very slight increase in tumors. After six months exposure of B-220+TPA in the B-220 group, B-220 was no longer administered (B). Immediately a rapid increase of tumors was seen. These results are illustrated in FIG. 4.

The initial DNA damage was there all the time, but was "silent" in the mice treated with B-220. Not even the very potent tumor promotion did have any effect with B-220 pretreatment. After the termination of B-220 treatment there was a rapid development of tumors indicating that both the initial DNA damage was present and the tumor promotor could catalyze the tumor formation. Tumor initiation was a genotoxic event and tumor promotion was an oxidative stress in this model.

These results show that B-220 is not a carcinogen in itself and further that B-220 can eliminate the effects of tumor initiations by the potent carcinogen DMBA and block tumor promotion by the potent tumor promotor TPA. When B-220 is removed the initial DNA damage can—together with a promotor—generate as much tumors as in the positive control. In other words, B-220 can, in vivo, switch on and off the tumor process.

EXAMPLE 11

Figure 5:
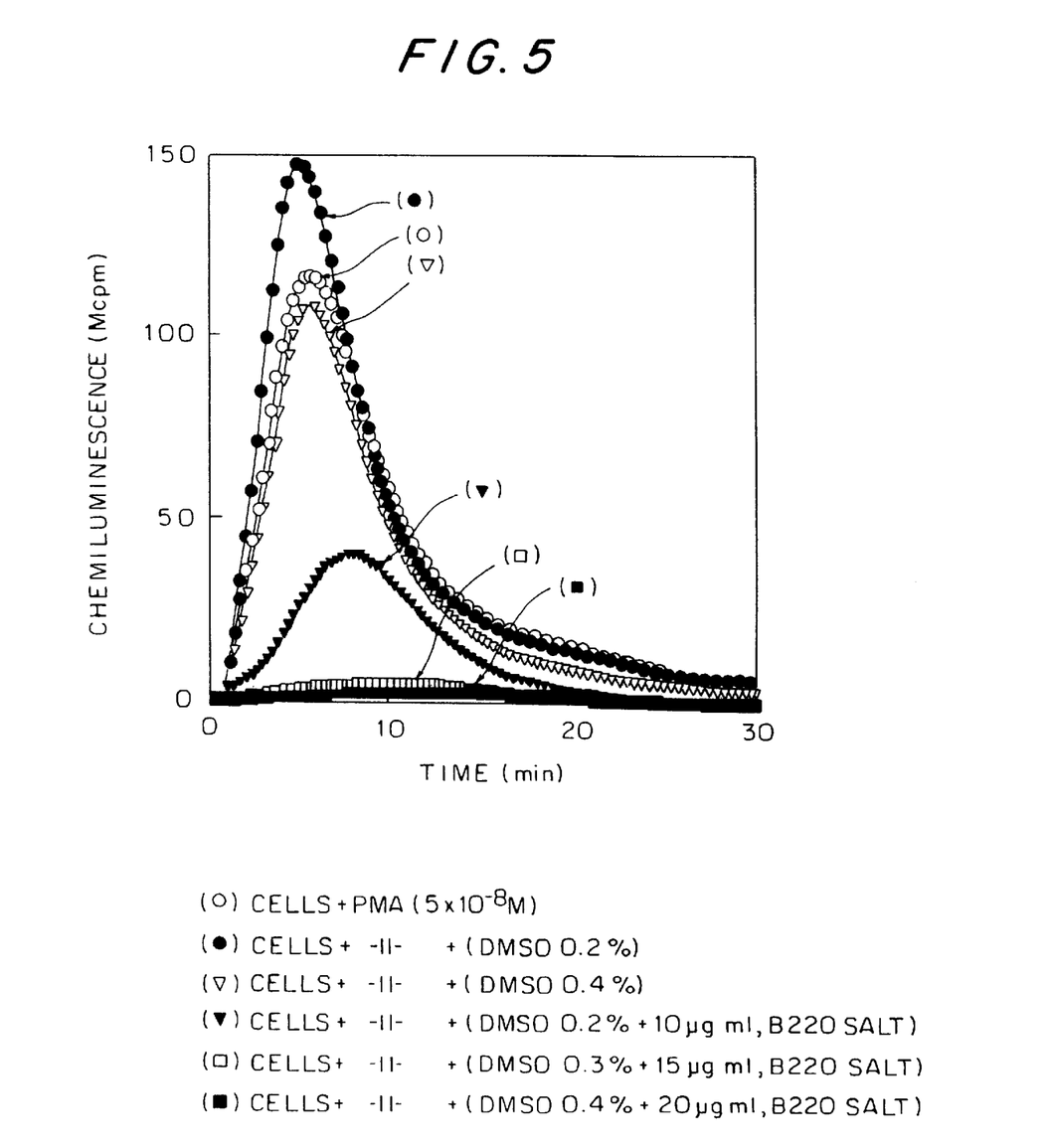
FIG. 5 illustrates that B-220 down-regulates and eliminates formation of hydrogen peroxide and superoxide ion generated by oxidase.

In this test the effects of "B220" have been exposed to human cell cultures of phagocytes. Luminol reacts with the markers for oxidative stress, hydrogen peroxide or the superoxide ion, and generates light. This light is measured as chemiluminescence as indicated in FIG. 5. The data in the figure shows that "B220" down regulates and even eliminates (in a dose dependent manner) the formation of hydrogen peroxide and superoxide ion, generated by oxidase. "B220" have the same effect both in the form of salt and the free base. The figure shows the intracellular inhibition of oxidase but the effects are also seen extracellular.

The consequence is that "B220" could be efficient to reduce or inhibit inflammatory processes, for instance over-reactions in the immune system, allergy, asthma etc. (cf. the general part on page 2 of the specification of this application).

HIV-patients have a number of processes on-going leading to AIDS. One of the more important is a release of oxygen related radicals from phagocytes. This is an early event and is combined with low levels of protecting agents (vitamins, antioxidants). This leads to lipidperoxidation, loss of cells, increased risk for tumor diseases and premature aging. The results shown in FIG. 5 indicate that "B220" can down-regulate/inhibit exactly this formation of oxidants in human phagocytes. "B220" has therefore a good useful to be a potential drug for HIV-patients, especially in combination with other characteristics/effects like low toxicity, anti-viral effects (see U.S. Pat. No. 4,990,510), inhibition of human HIV-integrase (see WO 96/00067), anti-cancer effects (U.S. Pat. No. 4,990,510) etc.

EXAMPLE 12

Figure 6:
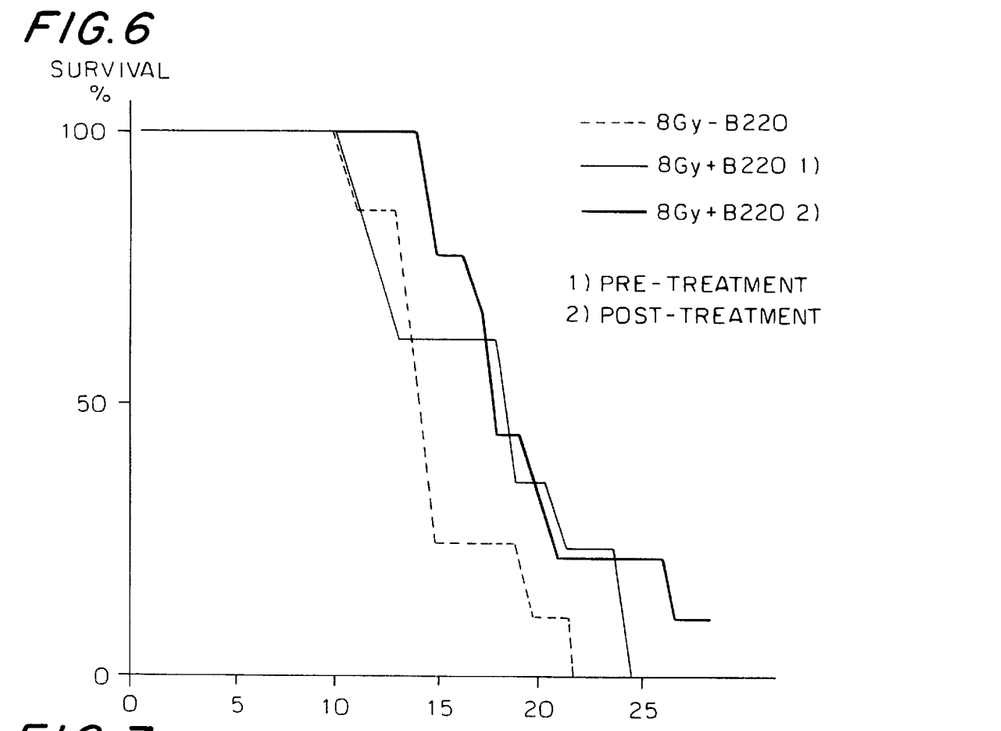
FIG. 6 shows results when mice were exposed to whole-body gamma irradiation and treated with B-220.

Gamma-irradiation is a very potent agent which induces oxidative stress, reduces body weight gain and shortens life span. In FIG. 6 results are shown when mice were exposed to whole body gamma-irradiation at high doses. The $LD_{50}$ for this strain of mice is 8 Gray (Gy) and in the experiment up to 14 Gy was used. The human $LD_{50}$ of gamma-irradiation is approx. 3 Gy.

"B220" was administered intra peritoneal in corn oil 24 and 3 h before the irradiation. At very high doses (14 Gy) "B220" had no protective effect while a protective effect was observed at 8 Gy, in terms of an increased life span. Interestingly, administration of "B220" after irradiation (8 Gy) also gave a protective effect similar to pre-treatment.

Figure 7:
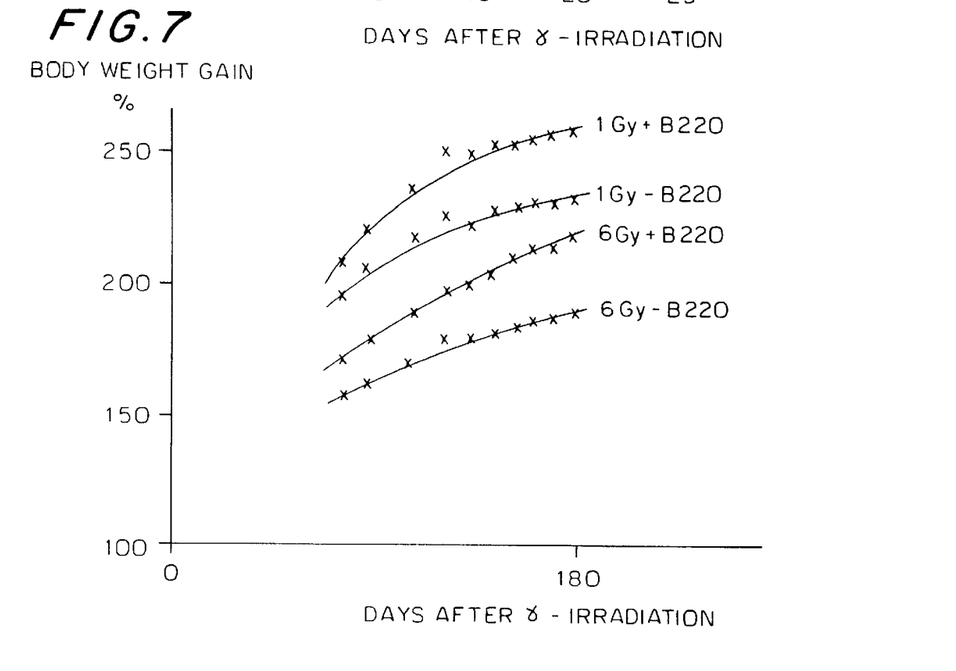
FIG. 7 shows the relationship between body weight gain and administration of B-220 for mice treated with gamma irradiation.

At lower doses an increased body weight gain was observed when "B220" was administered. FIG. 7 shows the comparisons between 1 and 6 Gy±"B220". The body weight gain of each group is shown as per cent of the body weight at the time of irradiation. A lower body weight gain is an indicator of a shorter life span in the long term perspective. Gamma-irradiation is a way to induce a premature aging which is also seen as gray fur of these mice.

HIV/AIDS patients suffer from the Dorian Gray syndrome, i.e. premature aging as well as loss of body weight. In both cases oxidative stress is likely to be an important factor. "B220" shows in this model, where whole body oxidative stress was induced by gamma-irradiation, a protective effect for both life span (increased) and body weight gain (increased). "B220" could therefore possibly be a protective agent for the treatment of HIV (see also U.S. Pat. No. 4,990,510 and WO 96/00067).

EXAMPLE 13

Figure 8:
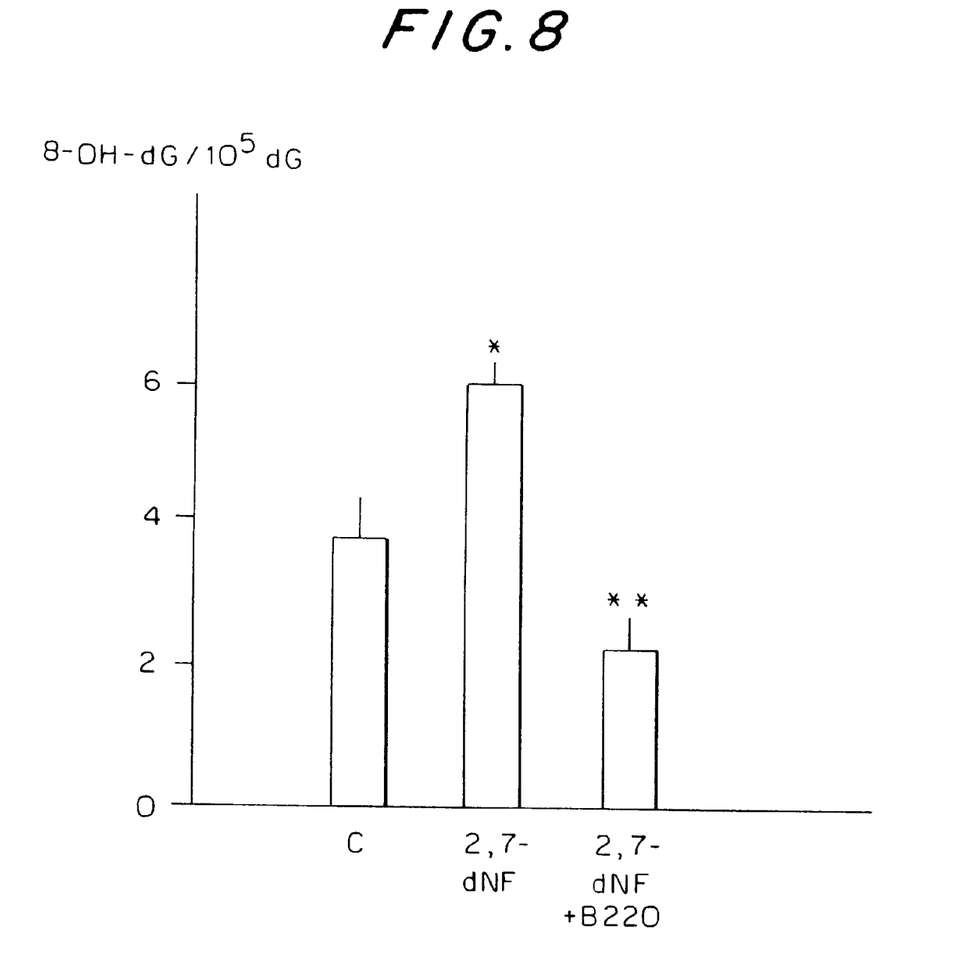
FIG. 8 shows the effects of dNF and dNF+B-220 upon rats exposed to urban air pollution.

Oxidation of deoxyguanosine (dG), one of the bases in DNA, is an oxidative lesion of DNA related to oxidative stress. The reaction product between free radicals and dG is 8-hydroxy-2'-deoxyguano-sine (8-OH-dG). This biomarker is a reaction product found in DNA, i.e. the oxidative stress is not only found as oxidants in the circulation or in the cytoplasm, but reaches the nucleus and reacts with DNA. In FIG. 8 results are shown when the urban air pollutant (result of incomplete combustion of fuels of vehicles) and carcinogen 2,7-dinitrofluorene (2,7-dNF) was administered orally to rats. In the metabolism reactive intermediates were formed that oxidized dG to 8-OH-dG When the rats were pre-treated with "B220" the oxidative stress was not only reduced, but down-regulated to levels lower than the controls.

In this experiment it is shown that chemicals found in the human environment (could be substances found in the air, food, life-style factors etc.) can induce oxidative stress in vivo. 2,7-dNF is a model substance for a large variety of chemicals including nitrated substances, amines and nitroso-amines. Many drugs belongs to this family of substances.

"B220" could therefore possibly protect the individual for oxidative stress induced by chemicals (for instance in the occupational environment). Further, "B220" could possibly protect for some side effects induced by certain drugs.

The results thus indicate that "B220" can be more efficient than substances used in terms of protection of tissue damage/oxidative stress. Further "B220" is efficient to protect tissues from oxidative damage initiated by toxic chemicals or situations similar to infarctions.

What is claimed is:

1. A method for treating oxidative stress selected from the group consisting of infections and inflammations comprising administering to a patient in need thereof an effective amount of a compound of the formula:

wherein $R_1$ represents hydrogen or from 1 to 4 substituents in positions 1–4 or positions 7–10, said substituents selected from the group consisting of halogen, $C_1$–$C_4$ alkyl groups, $C_1$–$C_4$ alkoxy groups, trifluoromethyl, and trichloromethyl, wherein in one of the positions 7–10 $R_1$ represents a hydroxyl group;

X is a group —$(CH_2)_n$—$R_2$, wherein $R_2$ represents a nitrogen containing basic residue selected from the group consisting of $NH_2$, $NHR_4$ and $NR_5R_6$, wherein $R_4$, $R_5$ and $R_6$ independently are lower alkyl or cycloalkyl and n is an integer of from 1 to 4, $R_3$ represents hydrogen, lower alkyl groups, lower cycloalkyl groups, and the physiologically acceptable addition products of the compounds with acids and halogen adducts.

2. The method according to claim 1 wherein the patient suffers from bronchial asthma or rheumatoid arthritis.

3. The method according to claim 1 wherein $R_1$ in positions 2 and 3 is methyl and in the other positions is hydrogen, and wherein X is $CH_2N(CH_3)_2$ and $R_3$ is hydrogen.

4. The method according to claim 1 wherein $R_1$ in positions 1–4, 7, 8, and 10 is hydrogen, $R_1$ in positions 2 and 3 is methyl, and $R_1$ in position 9 is hydroxyl, and wherein X is $CH_2N(CH_3)_2$ and $R_3$ is hydrogen.

5. The method according to claim 1 wherein the patient suffers from rheumatoid arthritis.

* * * * *

UNITED STATES PATENT AND TRADEMARK OFFICE
CERTIFICATE OF CORRECTION

PATENT NO. : 6,248,742 B1
DATED : June 19, 2001
INVENTOR(S) : Jan Bergman et al.

It is certified that error appears in the above-identified patent and that said Letters Patent is hereby corrected as shown below:

Title page,
Item [54], delete "(2,3B)" and insert therefor -- (2,3b) --;

Item [57], ABSTRACT, after the formula,
Line 1, delete "medicated" and insert therefor -- medicament --;
Line 2, delete "prompting" and insert therefor -- promoting --;
Line 3, delete "oxidating" and insert therefor -- oxidative --;

Column 11,
Line 12, delete "useful" and insert therefor -- potential --;
Line 13, delete "potential" and insert therefor -- useful --.

Signed and Sealed this

Second Day of April, 2002

*Attest:*

JAMES E. ROGAN
*Attesting Officer*     *Director of the United States Patent and Trademark Office*